United States Patent [19]

Spitz et al.

[11] 3,999,553
[45] * Dec. 28, 1976

[54] BIO-MEDICAL PRESSURE CONTROL DEVICE

[75] Inventors: Eugene B. Spitz; Richard E. Brenz, both of Media; Charles C. Hansford, Chester, all of Pa.

[73] Assignee: Bio-Medical Research, Ltd., Lima, Pa.

[ * ] Notice: The portion of the term of this patent subsequent to Aug. 26, 1992, has been disclaimed.

[22] Filed: June 18, 1975

[21] Appl. No.: 588,000

Related U.S. Application Data

[63] Continuation-in-part of Ser. No. 341,774, March 15, 1973, Pat. No. 3,901,245.

[52] U.S. Cl. .............................. 128/350 V; 137/510
[51] Int. Cl.² ...................................... A61M 27/00
[58] Field of Search ............... 128/350 V, 350 R; 137/510, 525

[56] References Cited
UNITED STATES PATENTS

| | | |
|---|---|---|
| 3,659,625 | 5/1972 | Coiner et al. ............... 137/510 X |
| 3,762,681 | 10/1973 | McKinney et al. ........... 137/510 X |
| 3,768,508 | 10/1973 | Schulte ....................... 137/525 X |
| 3,769,982 | 11/1973 | Schulte ....................... 128/350 V |
| 3,901,245 | 8/1975 | Spitz et al. ................... 128/350 V |

*Primary Examiner*—Dalton L. Truluck
*Attorney, Agent, or Firm*—Paul Maleson; Morton J. Rosenberg

[57] ABSTRACT

An improved cerebrospinal fluid anti-syphoning device for insertion into the human body to provide control and regulation of fluid being transported from the lateral ventricles to another portion of the body. The improved fluid anti-syphoning device includes a fluid housing member which is adapted to contain a pair of check valves which control fluid flow through the housing member and prevents back flow from a downstream area to an upstream area. A central chamber within the fluid housing member encloses a combination fluid egress conduit and flexible diaphragm which in cooperative relation provide for a substantial termination of fluid flow when the down stream pressure becomes too low with respect to the upstream pressure.

Specific construction of the fluid egress conduit and the flexible diaphragm provides for negation of possible terminal closure of the flow path through the anti-syphoning device under a wide range of conditions. The improved device includes a mechanism for manually actuating the flow through the outlet area of the housing member after the anti-syphoning device has been implanted within the human body.

16 Claims, 4 Drawing Figures

BIO-MEDICAL PRESSURE CONTROL DEVICE

This patent application is a continuation-in-part of U.S. Pat. application Ser. No. 341,774 filed Mar. 15, 1973 now U.S. Pat. No. 3,901,245.

CROSS REFERENCE OF RELATED REFERENCES

This application incorporates by reference U.S. Pat. No. 3,566,875 issued Mar. 2, 1971.

BACKGROUND OF THE INVENTION

1. FIELD OF THE INVENTION

The present invention pertains to medical devices. The instant invention relates to medical devices implanted within the human body. The subject invention pertains to devices being implanted within the human body for purposes of draining cerebrospinal fluid during the treatment of hydrocephallus. Further, the present invention relates to improved devices for controlling the fluid flow when the pressure differential between an upstream and downstream area may become sufficiently large.

2. PRIOR ART

Devices for draining cerebrospinal fluid are know in the art. However, in some prior devices one way check valves alone are incorporated to promote drainage of the cerebrospinal fluid. Such valves fluidly communicate with the brain area and other parts of the body. However, rapid decreases in the pressure of the parts of the body to which the fluid is being drained may cause substantial fluid to be transported from the brain in a manner which is too rapid. Such a condition may have deleterious results and possibly cause death of the patient where such prior devices have been implanted.

In some prior drainage devices there has not been included a mechanism whereby the fluid flow may be terminated when the downstream pressure of the body to which the fluid is being drained becomes too low with respect to the upstream fluid pressure. Such prior device did not provide automatic flow control of the fluid being drained from the brain area.

The device of which this improved system is based, provided for adequate control of the passage of cerebrospinal fluid from the brain under a wide variety of conditions. However, in some cases, it was found that under particular pressure differential conditions there resulted a closure of the mechanism to terminate flow through the device and provided a condition where it was difficult to open the valve mechanism subsequent to the termination of fluid flow. This may have deleterious results in that once the valve mechanism is closed there may be some time lag within which the valve remains closed.

SUMMARY OF THE INVENTION

An improved cerebrospinal fluid anti-syphoning device which includes a fluid housing mechanism having a central chamber. The fluid housing mechanism includes a flexible dome forming an upper surface of the central chamber. The flexible dome is adapted to be depressably displaced into the central chamber for increasing fluid pressure therein. An inlet mechanism which is in fluid communication with the central chamber is used for insertion of the fluid into the chamber. An outlet mechanism in fluid communication with the central chamber is used for transport of the fluid from the chamber. The antisyphoning device includes a fluid egress conduit mechanism which extends internal to the central chamber and is in fluid communication with the outlet mechanism.

A flexible diaphragm mechanism forms a lower surface of the central chamber and is positionally located adjacent and partially internal to the fluid egress conduit. The diaphragm is adapted to block flow of the fluid through the fluid egress conduit at a predetermined pressure differential between the inlet and outlet mechanisms. The improved cerebrospinal fluid anti-syphoning device further includes a diaphragm restraint which is secured to the housing and positioned below the diaphragm for preventing the flexible diaphragm from being externally displaced from the housing when the flexible dome is depressed. The diaphragm restraint is generally a plate member having at least one opening passing therethrough.

DESCRIPTION OF THE PREFERRED EMBODIMENTS

Figure 1:
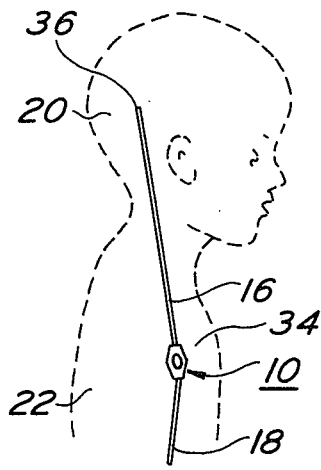
FIG. 1 is a view of the improved cerebrospinal antisyphoning device implanted within a human body.

Referring now to FIGS. 1–4 there is shown a cerebrospinal fluid anti-syphoning device 10 for insertion into the human body. In overall concept, device 10 in combination with upstream and downstream check valves to be described in following paragraphs, is used to control fluid flow passage of cerebrospinal fluid being transported from an upstream area 12 to a downstream area 14. Anti-syphoning mechanism 10 forms a means whereby cerebrospinal fluid pressure differential between upstream and downstream areas may be effectively monitored and controlled such that when the fluid pressure differential surpasses a predetermined value, the flow of the fluid passing through device 10 may be effectively terminated.

Generally, the pressure of the fluid entering inlet tube 16 is higher than the pressure of the fluid egressing from device 10 through outlet tube 18. This pressure differential provides for a flow of the fluid from upstream area 12 to downsteam area 14 through device 10. Where the pressure differential has been found to exceed certain predetermined values, excessive drainage of the fluid from the brain area 20 has been encountered. This excessive drainage of cerebrospinal fluid has in some cases caused irreparable damage to the patient being treated. Thus, it is the overall purpose of mechanism 10, as will be described in following paragraphs to monitor, control, as well as to terminate the flow of the fluid when the pressure differential between upstream area 12 and downstream area 14 exceeds a prescribed value.

The specific improvements to which anti-syphoning device 10 are directed include the problem of previous devices providing for a terminal closure and not permitting opening to provide continued flow once device 10 has initially terminated the flow due to a high pressure differential. Thus, improved anti-syphoning device 10 as herein described is directed to cyclically open and close dependent on the fluid pressure differential between upstream area and downstream area 12 and 14 respectively in a highly reliable manner. Although not clearly understood, it is believed that terminal closures of previous devices have been encountered due to a number of parameters. These parameters, include the inherent structure of the fluid closing and opening portions of device 10 as well as gravity effects on antisyphoning devices due to the various positionally orientations of human bodies 22 within which such devices are implanted. As is clearly seen, gravity effects would create various forces on the flow of fluid and such forces would in some cases be added to pressure differential forces and in some cases be subtracted from such pressure differential forces and in further cases would have no effect on the pressure differential forces of the flowing fluid.

It is to be understood that the device 10 includes upstream check valve 24 and downstream check valve 26 which are inserted respectively into upstream and downstream inlet and outlet areas 28 and 30. Valves 24 and 26 are generally similar in construction to those valves shown and described in U.S. Pat. No. 3,566,875 which is herein incorporated by reference. Check valves 24 and 26 described in the referenced patent include an inner elastic tubular member within an outer tube. Formed in the region of the downstream end of each inner tubular member is an axially extending slit which forms a valve opening. The valves automatically open when the pressure within each inner tubular member exceeds the pressure of the exterior thereof by a given amount. The reference slit automatically opens due to this pressure differential while automatically closing when the internal pressure is less than the external pressure of each tubular member by less than that pressure required to open the slit.

Figure 3:
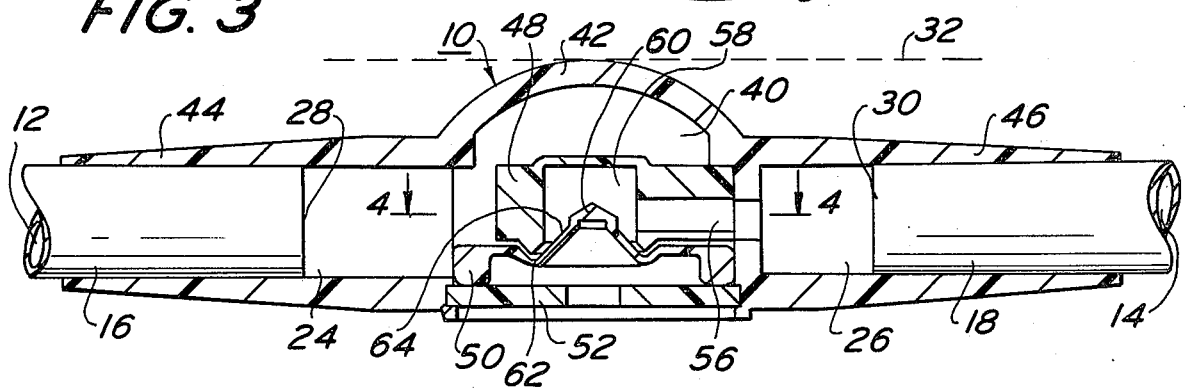
FIG. 3 is a cross section view of the anti-syphoning device being partially cut away; and, FIG. 4 is a sectional view of a portion on the improved anti-syphoning device taken along the section line 4—4 of FIG. 3.

Generally, anti-syphoning device 10 is positionally located within human body 22 and implanted adjacent to skin area 32 as shown in phantom lines of FIG. 3. Device 10 has been successfully implanted in the clavicle area 34 of human body 22 with inlet tube 16 passing to the general area of the lateral ventricles 36 within the skull for drainage of the cerebrospinal fluid therefrom. Outlet tube 18 of device 10 passes to some other portion of body 22 such as the peritoneal cavity to permit drainage of the fluid thereto. Positional placement of device 10 within human body 22 may be affected in a number of places and in some positional placements may be located nearer brain area 20 than the placement shown in FIG. 1 which is presented for illustration purposes only. However, specific positional placement of device 10 within body 22 is not important to the improvements in the inventive concepts as is herein described.

Cerebrospinal fluid anti-syphoning device 10 includes fluid housing member 38 having central chamber or cavity 40 through which the fluid flows. In overall contour, housing member 38 is similar in geometrical contour to a cylinder having appendages extending in opposing directions from a lateral side wall, however, such is not critical to the inventive concept as is herein described. In general, fluid housing member 38 may be formed of medical grade silicone rubber or some like material which is adaptable for insertion into human body 22. The only restriction on the material used for fluid housing 38 being that the material will not degrade within the environment where it is positioned or contaminate the body or fluid passing therethrough.

Fluid housing 38 is generally formed in one piece construction and includes flexible dome 42 which extends above central cavity 40 and essentially defines an upper surface of chamber 40. It will be noted that flexible dome 42 is adapted to be depressably displaced into central chamber 40 for increasing fluid pressure therein. As will be seen in following paragraphs, this increase in pressure may be used to prime the valving mechanism to provide the start up of fluid flow through device 10 or in some cases where for some inexplicable reason the valving mechanism is clogged and fluid flow has been terminated, depression of flexible dome 42 may provide for an opening of the valving mechanism to allow cerebrospinal fluid to pass through device 10. As can be seen in FIG. 3, the positional placement of device 10 such that flexible dome 42 is adjacent or contiguous to skin area 32 allows for flexible dome 42 to be depressed from external human body 22.

Inlet tube 16 is insertable within appendage 44 of fluid housing 38 and passes to inlet area 28 to permit fluid communication with central chamber or cavity 40 for insertion of the fluid passing from brain area 20 through inlet tube 16 into chamber 40. In similar fashion, outlet tube 18 is connected within outlet appendage 46 at outlet area 30 to provide fluid communication between outlet tube 18 and chamber 40. This allows for transport of the fluid within chamber 40 to pass down through outlet tube 18 to the peritoneal cavity or other area of the body so designated to receive the excessive cerebrospinal fluid being transported through device 10. Inlet and outlet tubes 16 and 18 respectively may be constructed of polyetheylene or some like material which would remain substantially inert with respect to the body environment within which they are implanted.

Figure 4:
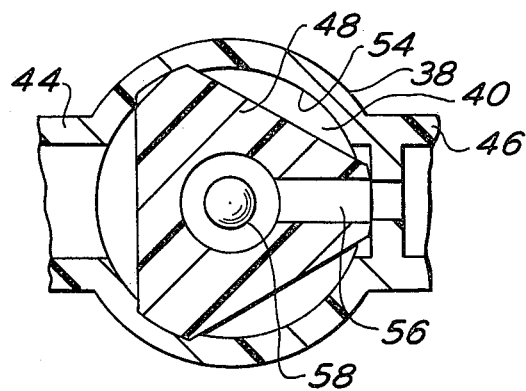

The basic anti-syphoning control and monitoring of fluid passing through devie 10 is provided by flexible diaphragm 50 and fluid egress conduit 48 mounted internal to central cavity 40 as is clearly shown in FIGS. 3 and 4. Operation of egress conduit 48 and flexible diaphragm 50 control and regulate the flow of fluid through device 10 responsive a predetermined pre-sure differential between upstream area 12 and downstream area 14 respectively.

Fluid egress conduit 48 extends internal to central cavity 40 and is in fluid communication with downstream area 14. Egress conduit 48 takes on the general geometrical contour of a truncated triangular cylinder with apexes approximately 120° apart. Egress conduit 48 is adhesively secured to otherwise fixedly mounted to inner surface 54 of fluid housing 38 within cavity 40 as is clearly shown in FIG. 4. Mounting of egress conduit 48 along the truncated apexes may be affected through bonding or some like mechanism such that conduit 48 is secured in positional relation within housing 38.

Egress conduit 48 includes pipe conduit 56 which is in fluid communication with downsteam check valve 26 and downstream area 14 as is shown. Egress conduit 48 further includes egress chamber 58 which is in cooperative relation with flexible diaphragm 50 and in fluid communication with pipe conduit 56. Egress chamber 58 and pipe conduit 56 in combination form a continuous passage which is generally L-shaped in contour. Thus, in combination, pipe conduit 56 and egress chamber 58 include a continous flow passage for fluid passing through chamber 40 from internal to chamber 40 to downstream area 14. Both egress chamber 58 and pipe conduit 56 are cylindrical in contour and chamber 58 may have a fluid volume greater than pipe conduit 56.

Flexible diaphragm 50 forms a lower inner surface of central chamber 40. Diaphragm 50 is positionally located adjacent and partially internal fluid egress conduit 48 within egress chamber 58. Diaphragm 50 is adapted to block flow of fluid through fluid egress conduit 48 when a predetermined pressure differential exists between the upstream and downstream areas 12 and 14 respectively. Flexible diaphragm 50 in overall contour is disc shaped and includes extension member 60 passing from an upper surface thereof which is partially inserted into egress chamber 58 of fluid egress conduit 48. In general, extension member 60 passes upwardly from recess 62 formed in a circular manner around and within an upper surface of flexible diaphragm 50. Recess 62 generally has a diameter which is substantially equal to the internal diameter of egress chamber 58. Thus, extension member 60 is substantially conical in contour and extends above a plane forming an upper surface of flexible diaphragm 50.

Conical extension member 60 is located substantially at the geometric center of flexible diaphragm 50 and extends partially into egress chamber 58 as is clearly shown in FIG. 3. Member 60 includes a conically shaped outer surface 64 for contacting a periphery of egress chamber 58 of fluid egress conduit 48 when a predetermined pressure differential between the inlet and outlet areas 12 and 14 are found to exist.

Thus, when the pressure differential betwen the inlet and outlet areas becomes excessive, conically shaped extension member 60 is movably displaced upwardly into contact with the periphery of fluid egress conduit chamber 58 to substantially terminate the flow of fluid from the inlet to the outlet areas. However, what has been found in use, is that by providing this particular mechanism, the fluid flow is never completely closed and thus some very minimal flow of fluid is seen to continually pass between the inlet and outlet sections 12 and 14. This mechanism has provided the particular improvement of stripping the terminal closure which has been found to occur in previous anti-syphoning devices.

Under normal conditions of flud flow from the inlet area 12 to the outlet area 14, flexible diaphragm 50 is displaced from egress conduit 48 when fluid is passing through improved anti-syphoning device 10 which generally results when the pressure differential between inlet section 12 and outlet section 14 is less than a predetermined value. However, when the pressure differential does exceed a predetermined amount, flexible diaphragm 50 is opposingly drawn into contiguous or substantially contiguous relation with the periphery of egress chamber 58 to effectively block the passage of fluid through fluid egress conduit 48.

Improved anti-syphoning device 10 includes diaphragm restraint 52 which is secured to fluid housing member 38 below flexible diaphragm 50. Restraint member 52 is displaced from diaphragm 50 through a predetermined distance to permit a flexible movement of diaphragm 50 in either an upward or downward direction. Restraint member 52 is generally secured to housing 38 through fixed securement such as bonding, insertion into a recess, or some combination of such securing mechanisms.

Figure 2:
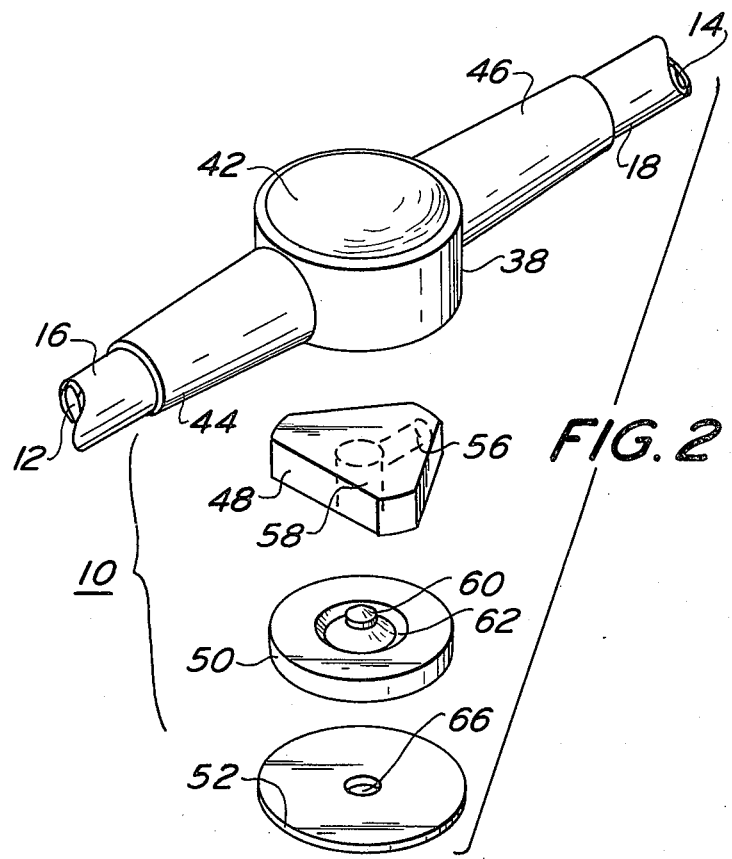
FIG. 2 is an exploded view of the improved antisyphoning device.

In general, flexible restraint member 52 may be a plate element having opening 66 passing therethrough. In overall contour, diaphragm restraint 52 is generally disk shaped and may be a plate member as is seen in FIGS. 2 and 4. Plate 52 may be constructed or formed of nylon or some like material which will remain essentially inert to the environment within which it is implanted and will not degrade within such an environment. Restraint member 52, shown for purposes of illustration as a plate in the accompanying figures, may also be formed in a grid type shape. The purpose of member 52 is to prevent flexible diaphragm 50 from being externally displaced or blown out of housing member 38 when dome 42 is compressed. When flexible dome 42 is manually or other wise depressed, a relatively high pressure is found to impinge upon flexible diaphragm 50 and may force it in a downward displacement where it contacts and is restrained through interaction with plate 52. Opening 66 in plate member 52 provides for the displacement of any fluid through such openings 66 when diaphragm 50 is downwardly displaced. This insures that flexible diaphragm 50 does not remain rigidly displaced with respect to plate member 52 through the damping of the fluid or other material therebetween, and permits free movement of flexible diaphragm 50 responsive to the fluid pressure.

Normal or conventional fluid pressure in brain area 20 of human body 22 is generally found to be equal to or greater than 200 mm of water. However, in the case of hydrocephallus, the fluid pressure in the brain may exceed normal values. For this reason upstream and downstream valves 24 and 26 provide a means whereby fluid may be drained from brain area 20. However, where the pressure in outlet or downstream area 14 becomes too low, excessive fluid may possibly be drained off and further, the drainage may be excessively rapid. Thus anti-syphoning device 10, within which valves 24 and 26 are inserted, is constructed to terminate the flow of cerebrospinal fluid when the down stream pressure becomes too low. Additionally, the improved anti-syphoning valve of the instant invention provides for a mechanism whereby terminal closure of the flow of fluid passing through device 10 is negated.

Through proper construction and postional relationships of flexible diaphragm 50 with respect to egress chamber 58, improved anti-syphoning device 10 can be provided to substantially termite or slow down fluid flow throughout a wide range of downstream pressures. Generally, improved device 10 is constructed to substantially terminate flow when the downstream pressure drops to 20–90mm of water. As an example, flexible diaphragm 50 has a thickness approximately within the range of 0.005–.01 and is so constructed as to be displaced from fluid egress conduit 48 approximately 0.004–0.020 inches when fluid is flowing therethrough. Further, as an example, plate member 52 may have an approximate thickness of 0.050 inches and include an approximate diameter of between 0.45 and 0.50 inches.

It is to be understood that the foregoing examples of dimensions and positional relations are used for illustration only and the control of fluid flow termination may be regualted over a wide range of pressures by changing construction and geometries. It is apparent that while the invention has been particularly shown and described with reference to a preferred embodiment thereof, various changes in form and detail may be made therein by those skilled in the art without departing from the spirit and scope of the invention.

What is claimed is:

1. An improved cerebrospinal fluid anti-syphoning device comprising:
   a. fluid housing means having a central chamber, said fluid housing means including a flexible dome forming an upper surface of said central chamber, said flexible dome adapted to be depressably displaced into said central chamber for increasing fluid pressure therein;
   b. inlet means in fluid communication with said central chamber for insertion of said fluid into said chamber;
   c. outlet means in fluid communication with said central chamber for transport of said fluid from said chamber;
   d. fluid egress conduit means extending internal said central chamber and in fluid communication with said outlet means;
   e. flexible diaphragm means forming a lower surface of said central chamber, said diaphragm means being positionally located adjacent and partially internal said fluid egress conduit means, said diaphragm means adapted to block flow of said fluid through said fluid egress conduit means at a predetermined pressure differential between said inlet and outlet means; and,
   f. diaphragm restraint means secured to said housing and positioned below said diaphragm means for preventing said flexible diaphragm means from being externally displaced from said housing means when said flexible dome is depressed, said diaphragm restraint means being a plate member having at least one opening passing therethrough.

2. The improved cerebrospinal fluid anti-syphoning device as recited in claim 1 where said flexible diaphragm means includes an extension member partially inserted into said fluid egress conduit means.

3. The improved cerebrospinal fluid anti-syphoning device as recited in claim 2 where said extension member is substantially conical in contour above a plane forming an upper surface of said flexible diaphragm.

4. The improved cerebrospinal fluid anti-syphoning device as recited in claim 3 where said conical extension member is located substantially at the geometric center of said flexible diaphragm means.

5. The improved cerebrospinal fluid anti-syphoning device as recited in claim 3 where said conically shaped extension member includes a conically shaped outer surface for contacting a periphery of said fluid egress conduit at said predetermined pressure differential between said inlet and outlet means.

6. The improved cerebrospinal fluid anti-syphoning device as recited in claim 3 where said conically shaped extension member is moveably displaced into contact with a periphery of said fluid egress conduit means at said predetermined pressure differential between said inlet and outlet means thereby substantially terminating flow of said fluid from said inlet to said outlet 7. The improved cerebrospinal fluid anti-syphoning device as recited in claim 3 where said conically shaped extension member is reversibly displaced into and out of contiguous contact with said fluid egress conduit means dependent on said pressure differential between said inlet and outlet means.

8. The improved cerebrospinal fluid anti-syphoning device as recited in claim 1 where said fluid egress conduit means is secured to an inner surface of said fluid housing means within said central chamber.

9. The improved cerebrospinal fluid anti-syphoning device as recited in claim 8 where said fluid egress conduit means includes a pipe conduit in fluid communication with said outlet means and an egress chamber in cooperative relation with said flexible diaphragm means and in fluid communication with said pipe conduit.

10. The improved cerebrospinal fluid anti-syphoning device as recited in claim 9 where said egress chamber has a fluid volume greater than said pipe conduit.

11. The improved cerebrospinal fluid anti-syphoning device as recited in claim 10 where said egress chamber and said pipe conduit in combination form a generally L-shaped contour.

12. The improved cerebrospinal fluid anti-syphoning device as recited in claim 1 where said flexible dome is formed in one-piece construction with said inlet and outlet means.

13. The improved cerebrospinal fluid anti-syphoning device as recited in claim 12 where said flexible dome, said inlet and outlet means is formed of silicone rubber.

14. The improved cerebrospinal fluid anti-syphoning device as recited in claim 1 where said diaphragm restraint means includes said plate member being displaced partially from an inner surface of said flexible diaphragm means.

15. The improved cerebrospinal fluid anti-syphoning device as recited in claim 14 where said diaphragm restraint means contacts said flexible diaphragm means at a peripheral boundary surface thereof.

16. The improved cerebrospinal fluid anti-syphoning device as recited in claim 15 where said plate member includes a through opening located at substantially the geometric center of said plate member.

* * * * *